(12) United States Patent
Ghahremani et al.

(10) Patent No.: US 7,033,367 B2
(45) Date of Patent: Apr. 25, 2006

(54) SLOTTED CATHETER GUIDE FOR PERPENDICULAR INSERTION INTO A CRANIUM ORIFICE

(75) Inventors: Fathali Ghahremani, New York, NY (US); Jamshid Ghajar, New York, NY (US)

(73) Assignee: Neurodynamics, Inc., New York, NY (US)

( * ) Notice: Subject to any disclaimer, the term of this patent is extended or adjusted under 35 U.S.C. 154(b) by 218 days.

(21) Appl. No.: 10/135,649

(22) Filed: Apr. 30, 2002

(65) Prior Publication Data

US 2003/0028199 A1 Feb. 6, 2003

Related U.S. Application Data

(63) Continuation-in-part of application No. 09/677,053, filed on Sep. 29, 2000, now abandoned, which is a continuation-in-part of application No. 09/290,332, filed on Apr. 12, 1999, now Pat. No. 6,206,885.

(60) Provisional application No. 60/081,696, filed on Apr. 14, 1998.

(51) Int. Cl.
  *A61F 11/00* (2006.01)

(52) U.S. Cl. .............................. 606/108; 128/DIG. 26; 604/264

(58) Field of Classification Search .................... 606/1, 606/108, 129, 96, 102, 185, 130; 128/DIG. 26; 600/424, 434, 585; 604/19, 158, 160, 164.01, 604/171, 198, 264, 523, 533; 408/72 R, 408/72 B; 30/286–295; 248/163.1, 432, 248/176.1, 186.1, 346.01, 346.05, 351
See application file for complete search history.

(56) References Cited

U.S. PATENT DOCUMENTS

| | | | |
|---|---|---|---|
| 4,435,174 A * | 3/1984 | Redmond et al. ............ 604/174 |
| 4,613,324 A * | 9/1986 | Ghajar ....................... 604/539 |
| 4,642,942 A | 2/1987 | Guhring |
| 4,821,716 A | 4/1989 | Ghajar |
| 4,931,056 A | 6/1990 | Ghajar |
| 4,998,938 A * | 3/1991 | Ghajar et al. ................ 606/130 |
| 5,137,288 A * | 8/1992 | Starkey et al. ................. 279/42 |
| 5,219,332 A * | 6/1993 | Nelson et al. .............. 604/528 |
| 5,242,428 A * | 9/1993 | Palestrant .................... 604/265 |
| 5,292,325 A * | 3/1994 | Gurmarnik ................... 606/108 |
| 5,300,080 A * | 4/1994 | Clayman et al. ............. 606/130 |
| 5,520,692 A * | 5/1996 | Ferrante ....................... 606/80 |
| 5,611,515 A | 3/1997 | Benderev et al. |
| 5,713,858 A * | 2/1998 | Heruth et al. .......... 604/288.02 |
| 5,833,666 A * | 11/1998 | Davis et al. ................. 604/180 |
| 5,833,693 A * | 11/1998 | Abrahami ..................... 606/96 |
| 5,938,686 A | 8/1999 | Benderev et al. |
| 5,948,002 A * | 9/1999 | Bonutti ....................... 606/232 |
| 6,206,885 B1 * | 3/2001 | Ghahremani et al. ......... 606/96 |

* cited by examiner

*Primary Examiner*—Glenn K. Dawson
(74) *Attorney, Agent, or Firm*—Levisohn, Berger & Langsam, LLP

(57) ABSTRACT

A catheter guide for controlling an angle of entry of a catheter into a human cranium at an angle of 90 degrees to the surface and allowing for easy removable of the catheter guide from the catheter after use. A tubular member defines a catheter guide lumen to permit the passage therethrough of a catheter. A base supports the tubular member. In a two piece assembly, the tubular member may have a fracture line allowing the catheter guide to be separated from the catheter. In an integrated, break-away assembly, the catheter guide may be broken apart to allow for the removal of the catheter guide from the catheter. Alternatively, in an integrated assembly or in a two piece assembly, the catheter guide may be removed from a catheter through a slot in the catheter guide.

7 Claims, 7 Drawing Sheets

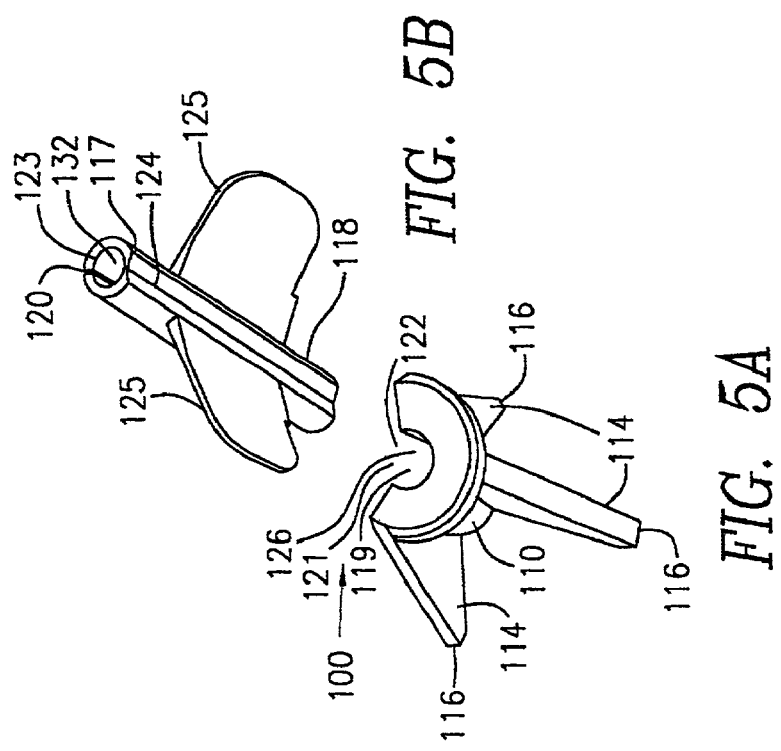
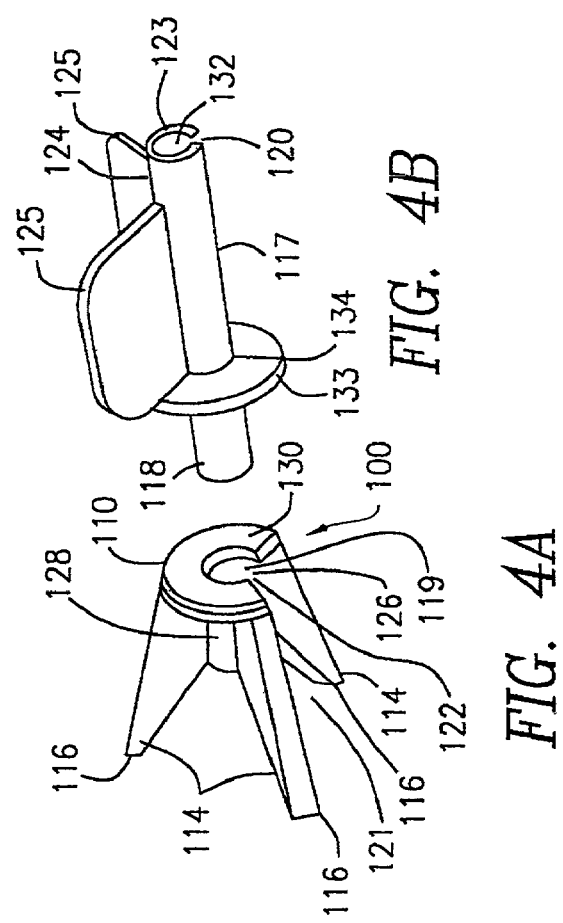

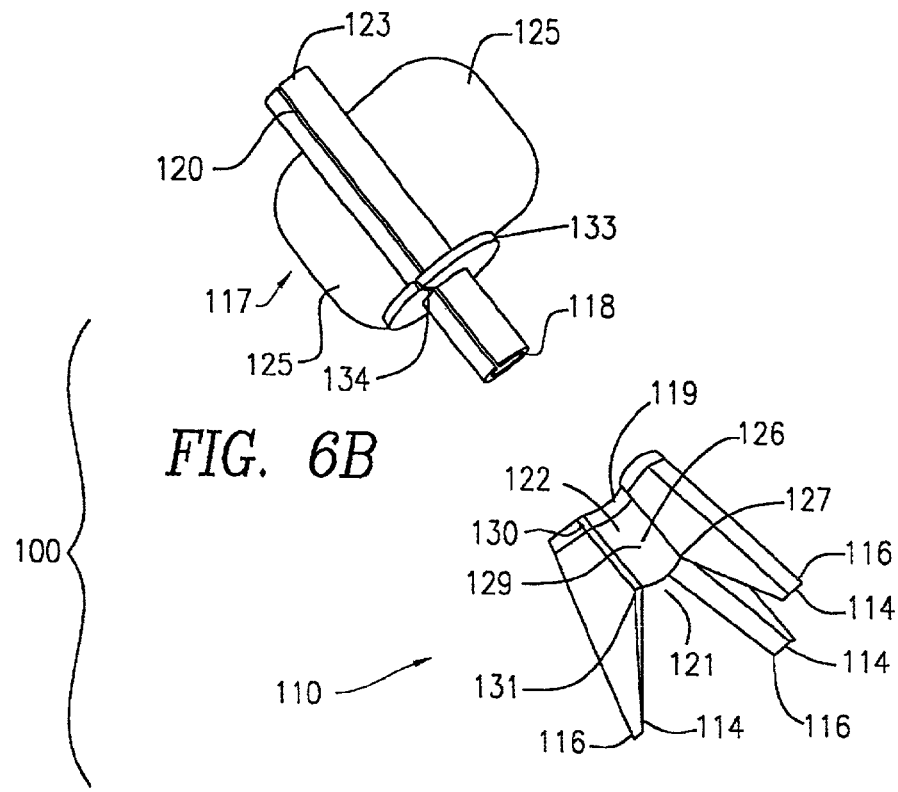
FIG. 6B
FIG. 6A
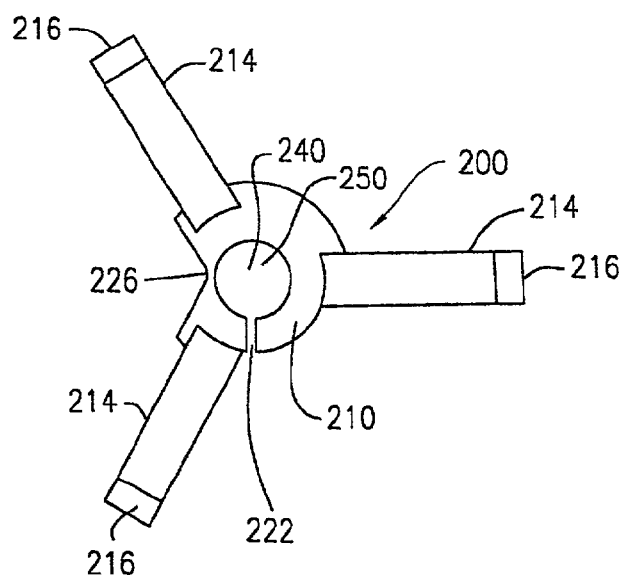
FIG. 7

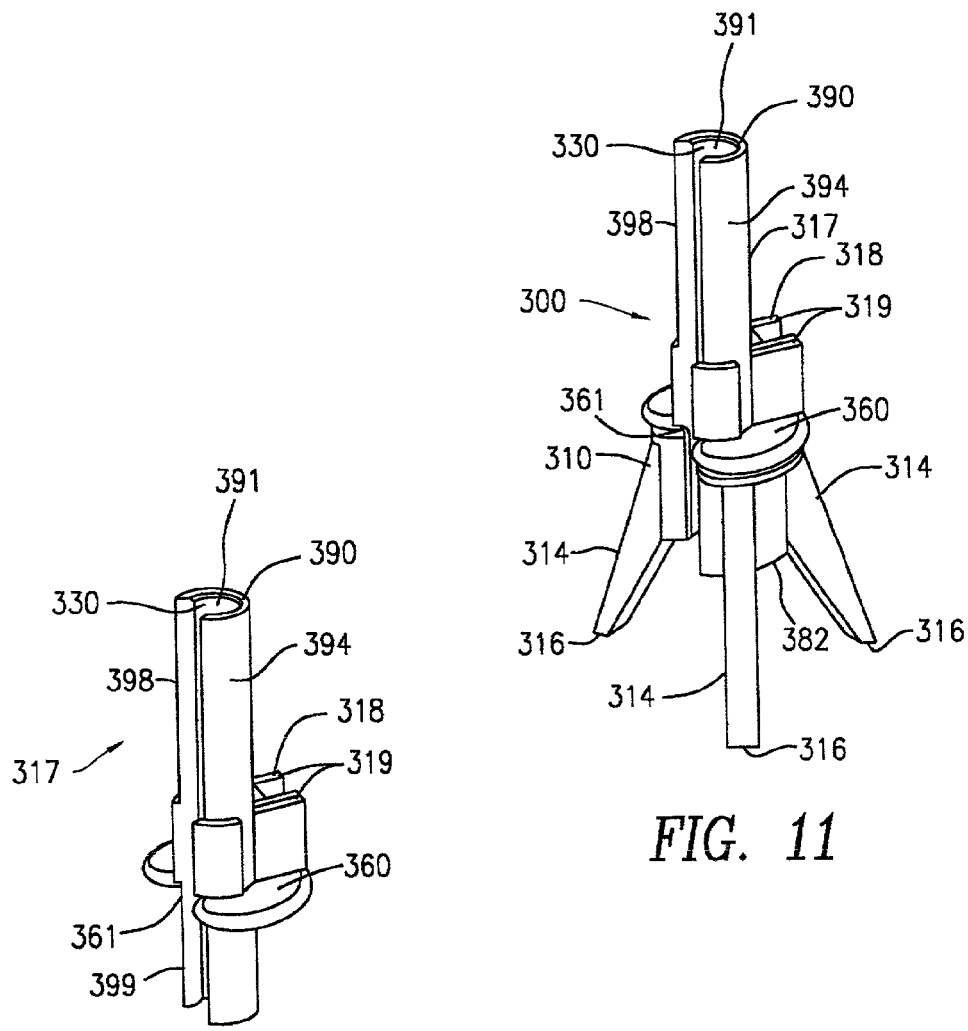
FIG. 11
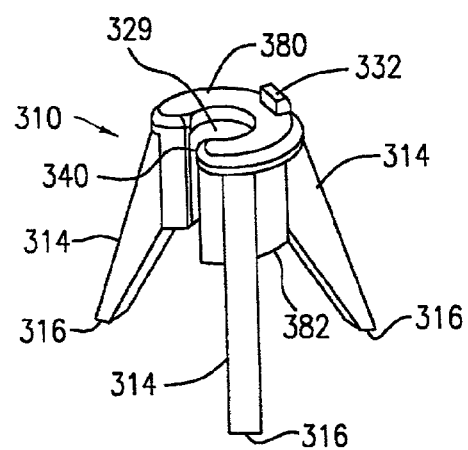
FIG. 12
FIG. 13

SLOTTED CATHETER GUIDE FOR PERPENDICULAR INSERTION INTO A CRANIUM ORIFICE

RELATED APPLICATIONS

This application claims priority of and is a continuation-in-part application to U.S. patent application Ser. No. 09/677,053 filed Sep. 29, 2000, abandoned, which claims priority of and is a continuation to U.S. patent application Ser. No. 09/290,332 filed Apr. 12, 1999, now U.S. Pat. 6,206,885, issued Mar. 27, 2001, which claims priority of U.S. Provisional Application Ser. No. 60/081,696, filed Apr. 14, 1998, and claims the benefit of the earliest filing date, pursuant to 35 U.S.C. § 120. The contents of all of the foregoing non-provisional applications are fully incorporated herein by reference.

FIELD OF THE INVENTION

The invention relates to a catheter guide for inserting a catheter into a human cranium at an angle of 90 degrees to the surface and for easy removal of the catheter guide from the catheter. More particularly, the invention relates to a slotted catheter guide for ventricular catheter placement where the catheter insertion is oriented at the correct angle of 90 degrees and where the catheter guide may be easily removed from the catheter.

BACKGROUND OF THE INVENTION

The four ventricles of the human brain are interconnected cavities that produce and circulate cerebrospinal fluid (CSF). Procedures involving ventriculostomy, i.e., placement of a catheter into the ventricular system of the brain, form a major part of a neurosurgeons clinical practice. General areas of application of ventricular catheter placement include intracranial pressure monitoring (ICP), draining or shunting of CSF, and the instillation of pharmacological therapeutic agents.

Intracranial pressure monitoring. i.e., the monitoring of ventricular pressure, is critical to the management of patients after severe head trauma, fulminant meningitis, Reyes' syndrome, encephalitis, stroke, cerebral hemorrhage, or subarachnoid hemorrhage producing stupor or coma. However, the ventricles are usually compressed after head trauma and thus they are technically difficult to cannulate for ICP monitoring. Thus, subarachnoid pressure monitoring, which is not as true a measure of cerebral pressure as intraventricular pressure monitoring, is generally used.

CSF drainage is essential for patients with congenital or acquired hydrocephalus. This procedure, which can only be performed with an intraventricular catheter, is a life-preserving step, because it can permanently reduce intracranial pressure. The ventricular catheter used to drain cerebrospinal fluid is connected to a peripheral subcutaneous drainage system, i.e., to the peritoneal cavity or systemic circulation via the heart. In hydrocephalus, the ventricles are enlarged and are an easier target for cannulation. However, reports in neurosurgical literature indicate that suboptimal placement in dilated ventricles can subsequently produce catheter obstruction when the ventricles decompress as the result of draining and become smaller, thus emphasizing the need for accurate placement.

Catheter placement in cerebral ventricles is widely performed on patients with carcinomatous and fungal meningitis for the administration of well-known anti-neoplastic and antifungal chemotherapeutic agents, respectively. Invariably, the ventricles in these patients are small or even if normal sized and difficult to cannulate.

Standard procedures for ventricular catheterization are disclosed in the textbook literature. See, for example, *Neurosurgery*, edited by Robert H. Wilkins and Setti S. Rengachary, Section A, Chapter 13, Techniques of Ventricular Puncture (McGraw Hill 1984) or *Patient Care in Neurosurgery*, Third Edition, Oyesiku, et al., Chapter 2, pages 32–43 (Little, Brown and Company 1990).

The most frequently chosen site for ventricular catheterization is the coronal region. In most cases, a catheter is inserted in the anterior horn of the lateral ventricle through an orifice or burr hole drilled just anterior to the coronal suture in the midpupillary line of the cranium, i.e., in the frontal bone over the ventricle. This is known in the field as Kocher's point. The burr hole need only be slightly larger than the diameter of the selected catheter to ensure a snug fit and provide a seal against CSF leakage and is placed approximately 1 cm. anterior to the coronal suture, approximately 10 to 12 cm. above the nasion, and approximately 2 to 3 cm. from the midline over the nondominant hemisphere. After the burr hole is made, the dura and underlying pia-arachnoid are opened, for example, with a fine-tipped blade or needle.

The lateral ventricles of the human brain form an arc parallel to the arc of the cranium, i.e., the contour of the lateral ventricles parallels the arc of the surface of the skull. Thus, a catheter guided perpendicular to the cranial surface at the point of entry into the cranium will enter the ventricular system. Specifically, any line penetrating a burr hole in the surface of the skull at a 90° angle also bisects the lateral ventricle.

Various methods have been utilized in the prior art in an attempt to ensure the correct placement of a catheter device in the patient's cerebral ventrical. One such method involves the use of a pre-measured catheter having a stylet which may be introduced and directed freehand through the burr hole, approximately in the coronal plane, and angled towards the medial canthus of the ipsilateral eye, using external landmarks such as the inner canthus of the eye in the frontal plane and a point just in front of the external auditory meatus in the lateral plane as guided to placement. CSF should flow freely from the catheter tip at a depth of approximately 4 to 5 cm. from the interior cranial surface.

A distinctive "give", or release of opposition, can often be felt when the ventricle is penetrated. Pressure should be measured at this point, however care should be taken, since an artificially low value will be obtained even if small amounts of fluid are lost. After removal of the stylet from the catheter, the catheter can be advanced another 1 cm. or so to insure placement in the frontal horn at a depth of about 5 to 6 cm. from the external table of the skull, care being taken that CSF continues to flow.

Intraoperative fluoroscopy and air ventriculography, well known techniques in the art, have been used to confirm freehand catheter placement. While these procedures can be helpful in placing the catheter if the ventricles are small, they also add to the complexity of the overall procedure.

Aside from the cost and time constraints of such radiographic confirmation of catheter placement, many published reports of postoperative studies have revealed misplacement of catheter tips in cerebral matter or subarachnoid space. This misplacement results in increased neurological morbidity and the need for additional operation time. Moreover, multiple passes of the catheter into cerebral matter are quite common before the ventricles are properly penetrated.

Finally, the anxiety a neurosurgeon experiences when trying to place a catheter by freehand into the ventricular system makes first pass success that much more difficult and further increases the risks involved in the procedure.

A procedure to ensure correct catheter placement was disclosed and claimed by one of the present applicants in U.S. Pat. No. 4,613,324 (the '324 patent), issued Sep. 23, 1986. The disclosure of that patent is therefore specifically incorporated herein by reference. The apparatus comprises a guide assembly which when positioned over an orifice drilled in the cranium above the anterior horn of the lateral ventricle, guides a catheter and obdurator through the orifice and into the lateral ventricle at an angle normal to an imaginary plane formed by a tangent to the cranium at the orifice.

The method of utilizing the claimed device of the '324 patent comprises providing an orifice in the cranium just anterior to the coronal suture in a midpupillary line of the cranium and inserting a ventricular catheter containing an obdurator through the orifice towards a lateral ventricle, wherein the catheter containing the obdurator is guided through the orifice, by means of a guide assembly, at an angle normal to an imaginary plane formed by a tangent to the cranium at the orifice.

This orientation of 90° is required for proper placement of the catheter within the ventricular portion of the patient's brain since, if the burr hole of 3.2 mm deviates by more than about 7 degrees from the perpendicular to a plane tangent to the point on the cranium where the catheter is inserted, the catheter will be directed away from the ventricular region and into other areas of the organ not conducive to the intended purposes of the apparatus disclosed. Thus, aligning the burr hole in such a precise manner greatly simplifies the subsequent task of correctly aligning the catheter within the ventricular cavity.

An apparatus to ensure drilling an orifice in the human cranium at an angle of substantially 90 degrees to a plane defined by a tangent to the surface of the cranium at the orifice was disclosed and claimed by the present applicants in U.S. Pat. No. 4,821,716 (the "'716 patent"), issued Apr. 18, 1989. The disclosure of that patent is therefore specifically incorporated herein by reference. The apparatus of the '716 patent comprises a drill guide assembly means which, when positioned over the cranium provides a means for guiding a drill used for making an orifice in the cranium.

An apparatus for accurately inserting a catheter through an orifice in the human cranium and guiding said catheter into a ventricle of a human brain was disclosed and claimed by one of the present applicants in U.S. Pat. No. 4,931,056 (the "'056 patent"), issued Jun. 5, 1990. The disclosure of that patent is therefore specifically incorporated herein by reference, as well. The apparatus of the '056 patent comprises a first guide means adapted to rest on the human cranium and a catheter guide means inserted within the first guide means.

In using the prior apparatus, visualizing the drill and catheter within the guide assemblies can be intricate and/or difficult. It was therefore desirable to present improved apparatus and methods to further assist in visualizing the drill and the catheter within the guide assemblies. Accordingly, U.S. Pat. No. 6,206,885 issued Mar. 27, 2001 addresses this difficulty in the prior art, and describes a catheter guide and drill guide apparatus for visualizing the guiding of the drill (for perforation of the patient's cranium at an angle of substantially 90 degrees to the surface) and for visualizing the guiding of the accurate insertion and placement of a ventricular catheter by providing a drill guide and catheter guide with slots which are alignable.

Removing the catheter guide from the catheter can sometimes be difficult, awkward or time consuming. It is therefore desirable to present a new catheter guide that facilitates the easy removal of the catheter guide from the catheter.

SUMMARY OF THE INVENTION

It is an object of the present invention to provide a catheter guide allowing for controlling an angle of entry of a catheter into a human cranium at an angle substantially 90 degrees.

It is another object of the invention to provide a catheter guide allowing for ease in removal of the catheter guide from the catheter.

It is a further object of the present invention to provide a tubular member allowing for ease in removal of the tubular member from the catheter.

It is a further object of the present invention to provide a base for holding a tubular member, through which a catheter may be placed.

The above and other objects are accomplished by the invention, which includes a catheter guide with a slot, which allows for entry of a catheter into the human cranium at an angle of substantially 90 degrees.

In one embodiment, the catheter guide includes a tubular member non-removably connected to a base and the assembly has a slot along its height. The slot is sufficiently wide to allow for the easy removal of the catheter guide from the catheter.

In another embodiment, a catheter guide includes a tubular member having a cylinder shaped wall defining a central channel and the tubular member is removably connectible to a base having a central lumen. When the tubular member and base are connected, the central channel and central lumen are contiguous to form a common central lumen. Preferably, the tubular member is connected to the base by the tubular member being inserted into the base. A catheter may be inserted through the common central lumen. The base also has a side opening. The tubular member has a slot along its height, two wings on the outside of its wall and a break-away line along the height of the tubular member and between the two wings. The break-away line is on the opposite side of the two wings from the slot in the tubular member. Once the catheter is placed in the ventricles of the patient, the tubular member may be disengaged from the base separating the two components. Then the base may be removed from the catheter using the side opening of the base. The tubular member then may be split apart into two pieces by pressing on the wings causing a split along the break-away line and thus breaking the tubular member into two pieces with the pieces separating from each other from the break-away line to the continuous slot and thus allowing the catheter guide to be broken away from the catheter after use of the catheter guide.

In another embodiment a catheter guide includes a tubular member molded to a base and the integrated assembly has a common central lumen through which a catheter may be inserted. The assembly has a thin slot along its height, a break away line along its height and two wings. The break away line is situated between the two wings and on the opposite side of the wings from the slot, such that when the two wings are pressed together the assembly splits into two pieces, from the break away line to the slot, and thus the catheter guide may be easily removed from the catheter.

In another embodiment, the catheter guide includes a tubular member removably connected to a base and the assembly has a slot along its height. The slot is sufficiently wide to allow for easy removal of the catheter guide from the catheter.

BRIEF DESCRIPTION OF THE DRAWINGS

The method and apparatus of the present invention will now be described with reference to the accompanying drawing figures, in which:

FIGS. 4A and FIG. 4B are is a side perspective views of an embodiment of applicants' break-away catheter guide, showing in FIG. 4A a base portion, and in FIG. 4B a separate insert portion with wings.

FIG. 5A and FIG. 5B are rear perspective views of applicants' break-away catheter guide of FIG. 4, showing in FIG. 5A a base portion from a rear view and showing in FIG. 5B a separate insert portion with wings.

FIG. 6A and FIG. 6B are front perspective views of applicants' break-away catheter guide of FIG. 4, showing in FIG. 6A a base portion with a slot clearly visible and showing in FIG. 6B a separate insert portion with wings.

FIG. 7 is a bottom plan view of an embodiment of an integrated break-away catheter guide.

FIG. 11 is a side perspective view of an embodiment of applicants' two-piece connectible catheter guide including a tubular member removably connected to a base.

FIG. 12 is a side perspective view of the tubular member of applicants' catheter guide of FIG. 11.

FIG. 13 is a side perspective view of the base of applicants' catheter guide of FIG. 11.

DETAILED DESCRIPTION OF THE PREFERRED EMBODIMENTS

Figure 1:
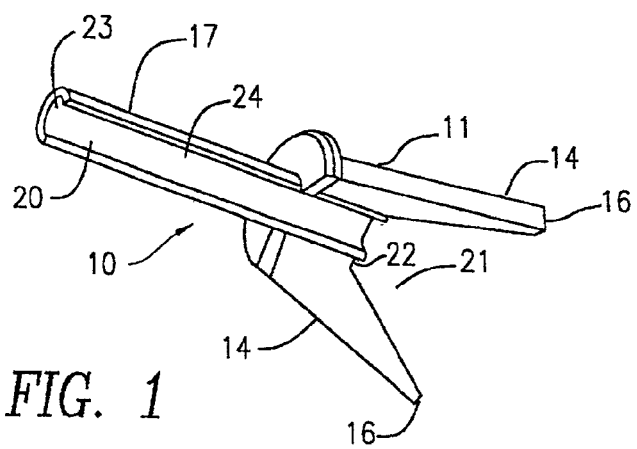
FIG. 1 is a front perspective view of an embodiment of applicants' integrated catheter guide wherein a slot is clearly shown.
Figure 2:
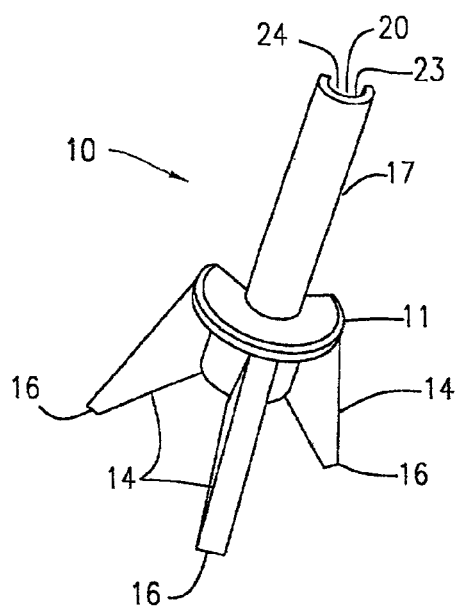
FIG. 2 is a rear perspective view of applicants' integrated catheter guide of FIG. 1 wherein most of a slot is hidden from view.
Figure 3:
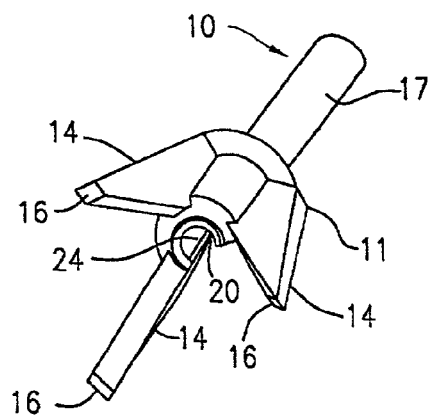
FIG. 3 is another perspective view of applicants' integrated catheter guide of FIG. 1.

Turning initially to FIGS. 1 through 3, there is illustrated an integrated catheter guide 10 for controlling the entry of a ventricular catheter (not shown) at a preferred angle of substantially 90 degrees into a burr hole through the cranium of a patient (not shown). The initial function of catheter guide 10 is to control the angle of entry of the catheter during its insertion into the perforation of the cranium, especially at the start of the catheterization procedure. Catheter guide 10 may be seated, for example, directly upon the scalp of the patient, above the bore hole.

Alternately, in the event a larger incision is made and catheter guide 10 is seated directly upon the surface of the skull, its legs spread apart the surrounding scalp tissue and prevent such tissue from being gathered or drawn to the burr hole during the catheterization procedure. Catheter guide 10 is thus preferably constructed of a rigid, non-deformable material such as a rigid engineering plastic in order to fulfill these functions. Also, clear plastic may be used to construct the catheter guide in order to allow for visibility through the catheter guide. The entire apparatus may be manufactured inexpensively from a plastic material, as a disposable assembly, thus reducing the cost of the assembly and assuring a sterilized catheter guide for each procedure.

As shown in FIG. 1, catheter guide 10 is a single, integral unit. Catheter guide 10 comprises base 11 and insert or tubular member 17 defining a central lumen or internal passageway 24. In the embodiment shown in FIG. 1 the tubular member 17 has a "C" shaped wall that defines a top opening 23, the central lumen or internal passageway 24 and a catheter guide slot 20 which is formed by the opening along the length or height of the "C" shaped wall of the tubular member 17.

Catheter guide 10 is formed so that base 11 and insert 17 are integrated into a one piece catheter guide by appropriate means, such as, molding the base 11 and insert 17 together. The insert 17 has catheter guide slot 20 through its entire length or height and catheter guide slot 20 is of sufficient width to allow for removal of the catheter guide from a catheter.

Extending from base 11 in a diverging manner are three legs 14, which terminate in free ends 16. Free ends 16 of legs 14 define a triangle lying within a defined plane. As illustrated in FIG. 1, the base 11 has a cut-out or base opening 22 between two of the legs. Between those two legs a leg space 21 is formed such that the base opening 22 and the leg space 21 are a contiguous space with the catheter guide slot 20 to allow for the easy removal of the integrated catheter guide 10 from a catheter inserted therethrough. The base opening 22 and leg space 21, together with the catheter guide slot 20, also allow for visualization of the catheter in the catheter guide 10.

Insert 17 acts as a guide means for guiding the catheter in a direction perpendicular to the plane defined by the triangle formed by legs 14 and through the geometric center thereof. The insert 17 or guide means is tubular and extends through base 11 in a direction perpendicular to the triangular plane described above.

Thus, insert or tubular member 17 is hollow and a defines the central lumen 24 to permit the passage therethrough of a ventricular catheter. The diameter of this lumen is not critical but it must, at a minimum, be sufficient to permit the passage of the catheter and it must, at a maximum, not be too large to prevent holding the catheter in its proper position. In accordance with the invention, insert 17 is provided with a catheter guide slot 20, which is an opening, along the entire length or height of the tubular member 17. The catheter guide slot 20, together with the leg space 21 and base opening 22, allow the neurosurgeon to have direct visual access to the burr hole, as well as to the catheter and allows for the removal of the catheter guide from the catheter. Thus, the tubular member 17 and base 11 form one integral piece, a contiguous, integrated assembly, the catheter guide 10.

When catheter guide 10 is placed on the patient's cranium with the free ends 16 of legs 14 resting thereupon, the plane of the triangle defined by free ends 16 coincides with or is parallel to a plane tangent to the cranial surface directly below insert 17. Accordingly, when a catheter (not shown) is placed within the central lumen 24, the catheter guide 10 directs the catheter perpendicular to this tangential plane, ensuring its entry into the burr hole through the cranial bone at an angle of substantially 90 degrees to the surface of a plane tangent to the cranium. This alignment assures that a ventricular catheter, inserted into the brain in a direction perpendicular to the curvature of the cranium, will not deviate from a preferred course. As noted above, if the orientation of the bore hole deviates by more than about 7 degrees from the perpendicular to a plane tangent to the cranium at the point of insertion of the catheter, the catheter is much more likely to be misaligned and to miss the ventricular portions of the brain entirely.

Preferably, legs 14 of catheter guide 10 are of equal length, equidistantly spaced and symmetrically disposed relative to each other, whereby the free ends 16 define an equilateral triangle. Insert 17 directs the catheter perpendicular to the plane defined by this equilateral triangle at the geometric center thereof and hence, perpendicular to the tangent plane upon the surface of the patient's cranium.

It is however, nevertheless possible to practice the invention with a catheter guide 10 having an asymmetric arrangement of legs 14, as long as the guide means, i.e., insert 17 of catheter guide 10, extends perpendicularly to the plane defined by the free ends 16 of legs 14, the catheter guide 10 is placed on the cranial surface such that this plane coincides with or is parallel to a plane tangent to the cranium at the orifice and that the leg space 21 formed between two of the legs and the base opening or cut-out 22 in the base are contiguous with the catheter guide slot 20 and of sufficient width to allow the removal of the catheter guide insert from the catheter.

Similarly, the invention may be practiced with a catheter guide 10 having more than three legs, as long as the above-described directional and space criteria are maintained. For example, a cone shaped support with cut-out can be used instead of legs. Additionally, while insert 17 is illustrated as being cylindrical in shape, any shape which allows an unencumbered passage of the catheter therethrough, but which maintains the catheter securely in position in use and yet allows for the removal of the catheter guide through the catheter guide slot and base opening from the catheter may be employed.

The height of catheter guide 10 and the distance between free ends 16 of legs 14 may be varied, as long as the following principles are observed. First, the base portion of catheter guide 10 must preferably form an equilateral triangle defined by free ends 16 of legs 14. Secondly, a line passing through the central lumen of insert 17 must be normal to the plane of the triangle thus defined and must pass through the geometric center thereof. Furthermore, the internal diameter of the central lumen may be varied as long as the lumen is constructed of a sufficient width to accept the catheter to be inserted therethrough and to hold the catheter in place. In an alternative embodiment of the invention, insert 17 of catheter guide 10 may be constructed having a length sufficient to pass completely through the base 11 and at least partially into the burr hole.

Preferably, the distance between free ends 16 of legs 14 ranges from about 1 cm to about 6 cm. The lower limit is established based on the smallest burr hole or orifice necessary for passing a catheter therethrough. These catheters may range from about 2–5 millimeters in diameter. The upper limit is established based on the change in skull curvature which occurs when the midline of the skull is crossed.

Thus, the embodiments shown in FIGS. 1 through 3 are that of the integrated catheter guide with slot. The advantages of the embodiment of the invention shown in FIGS. 1 through 3, include by way of example, the simplified usage of a catheter guide with slot which allows for the easy removal of the catheter guide from catheter. Since most ventricular catheters are a single size, by integrating the base and insert the physician or user is relieved of the chores of selecting the appropriate lumen to fit the base to the insert and discarding any un-used components. There is an additional advantage of cost saving in that the single piece embodiment shown in FIGS. 1 through 3 reduces packaging cost and wastage and savings will be realized throughout the medical system.

Turning now to FIGS. 4A and B through 6A and B, there is illustrated another embodiment of the present invention of a catheter guide 100 for controlling the entry of a ventricular catheter (not shown) at a preferred angle of 90 degrees into a burr hole through the cranium of a patient (not shown). The initial function of catheter guide 100 is to control the angle of entry of the catheter durin insertion into the perforation of the cranium. Catheter guide 100 may be seated upon the cranium in the same manner as catheter guide 10. Catheter guide 100 may also be constructed the same materials used to form catheter guide 10.

As shown in FIGS. 4A and B through 6A and B, in an embodiment of the invention, catheter guide 100 comprises base 110, having a "C" shaped side wall 128 connected to a "C" shaped top wall 130 and to a "C" shaped bottom wall 131 to form a top opening 119, a bottom opening 127, a side base opening 122, and a channel 129 between the "C" shaped top wall 130 and the "C" shaped bottom wall 131.

Catheter guide 100 further comprises an insert, guide means or tubular member 117 having a top end 123. The insert or tubular member 117 has a slot or opening 120 along its entire length or height. As shown in FIG. 4B, the insert 117 is also provided with a break-away or fracture line 124 and two wings 125 attached on either side of the break-away or fracture line. The width of the slot 120 is not critical, since the function of the slot 120 in catheter guide 100 is to provide a length of separation along the length or height of the tubular member 117 that allows the tubular member 117 to be broken apart when the two wings 125 of tubular member 117 are pressed together causing a separation along the break-away line 124.

Catheter guide 100 is formed so that base 110 and insert 117 are two separate pieces that may be connected by the user pressing the lower end 118 of insert 117 into the top opening 119 of base 110 and into the channel 129 of the base so that the side wall 128 securely holds the insert 117 in place in the channel 129.

In the embodiment shown in FIGS. 4A and B, the tubular member 117 has a platform 133 that is attached or molded to the outside of tubular member 117 so that it does not overlay the break-away line 124 or the slot 120. In the embodiment shown in FIG. 4, the platform 133 has a platform slot 134. The platform 133 forms a stop that prevents the tubular member 117 from further descending into the channel 129 in the base 110. Thus, the platform 133 rests on top of the "C" shaped top wall 130 of the base 110. The platform 133 may be provided with a notch and the "C" shaped top wall 130 may be provided with a protrusion that mates with the notch to snap together the tubular member 117 to the base 110. The protrusion on the "C" shaped top wall 130 may be released from the notch on the platform 133 to remove the base 110 from the insert or tubular member 117. In the embodiment shown in FIG. 4 the platform 133 is situated below the wings 125 and the platform slot 134 is contiguous with the slot 120, so that when the tubular member 117 is broken apart, the platform 133 does not interfere with the breaking apart of tubular member 117. The platform 133 is an example of one means that may be used to secure the tubular member 117 in its proper position in the base 110. The shape of the base 110 may also be varied so long as the base 110 meets the requirements for directing the catheter perpendicular to the curvature of the cranium and the base is equipped with a suitable opening to allow for its easy disengagement from the tubular member 117 and the catheter.

The insert or tubular member 117 is hollow and has a tubular channel or tubular central lumen 132, which extends throughout its length or height and tubular member 117 defines a tubular central lumen 132 to permit the passage therethrough of a ventricular catheter. The diameter of this lumen is not critical but it must, at a minimum, be sufficient to permit the passage of the catheter and it must, at a maximum, not be too large to prevent the catheter from being held in its proper position.

In use, the base 110 and insert 117 are connected to each other by inserting the lower end 118 of insert 117 into the base channel 129 so that the lower portion of the tubular channel 132 lies within the channel 129 in the base 110, thus forming a passageway for the catheter. In use the base 110 and insert 117 are connected prior to the insertion of a catheter into the catheter guide 100.

Extending from base 110 in a diverging manner are three legs 114. The free ends 116 of legs 114 define a triangle lying within a defined plane. As illustrated in FIG. 6, the base 110 has a cut-out or side base opening 122 between two of the legs which is of sufficient size to allow the removal of all catheters through it easily. Between the two legs, one on each side of the side base opening 122, a leg space 121 is formed. Thus, the side base opening 122 and the leg space 121 form a contiguous space with each other, or base slot 126.

Insert 117 acts as a guide means for guiding the catheter in a direction perpendicular to the place defined by the triangle formed by legs 114 and through the geometric center thereof. The insert 117 extends through base 110 in a direction perpendicular to the triangular plane described above, when the base 110 and insert 117 are connected. In the same manner as described above with respect to catheter guide 10, when catheter guide 100 is placed on the patient's cranium with the free ends 116 of legs 114 resting thereupon, the plane of the triangle defined by free ends 116 coincides with or is parallel to a plane tangent to the cranial surface directly below insert 117. Accordingly, when a catheter (not shown) is placed within the tubular channel 132, the catheter guide 100 directs the catheter perpendicular to this tangential plane, ensuring its entry into the burr hole through the cranial bone at an angle of substantially 90 degrees to the surface of a plane tangent to the cranium. This alignment assures that a ventricular catheter inserted into the brain in a direction perpendicular to the curvature of the cranium will not deviate from a preferred course.

Preferably, the two wings 125 are of substantially the same size and configuration, but the specific size and configuration of the two wings is not critical provided that the two wings do not interfere with the insertion or removal of the catheter into the catheter guide 100 or the insertion of the tubular member 117 into the base 110 and are of sufficient size to allow an operator to grasp each wing 125 firmly for purposes of pressing the two wings 125 together to cause a separation of the tubular member 117 along the break-away or fracture line 124 when the operator desires to disengage the tubular member 117 from the catheter. The two wings 125 may be molded onto the outside of the tubular member 117 and are attached on either side of the break-away line or fracture 124 of the tubular member 117 to allow the operator to exert sufficient pressure on the two wings to create a separation in the fracture line 124 when the operator desires to disengage the tubular member 117 from the catheter.

The break-away line 124 is a line, groove or indentation along which the insert 117 may be readily broken into two pieces when the wings 125 are pressed together each in the direction toward the break-away line 124. The pressing of the wings 125 together creates a separation along the break-away line 124 and because there is a separation at the slot 120, pressing the wings 125 together, thus divides the insert 117 into two broken pieces, each lying between the break-away line 124 and the slot 120. Thus, breaking the catheter guide allows the insert to be removed from a catheter inserted therethrough. The break-away line 124 extends the entire length or height of the insert 117 and may be constructed as a groove along the length or height of insert 117 that forms a weakened portion of the insert 117, yet which does not physically separate the insert 117, unless pressure is placed on the wings, which then allows the insert 117 to be broken apart into two pieces.

The legs of catheter guide 100 may be formed in the same manner, structure and positioning or with the cone-shaped support with cut-out instead of legs, as that described with respect to the catheter guide 10. Also, the height of the assembled catheter guide 100 should be similar to that described for the catheter guide 10.

Thus, in use the base 110 and insert 117 are assembled to form the catheter guide 100 by pressing together the base 110 and insert 117 prior to insertion of the catheter through the lumen of the insert 117. The catheter guide 100 is placed on the patient's cranium in the same manner as that described above with respect to the catheter guide 10 to allow for an alignment that assures that a ventricular catheter is inserted into the burr hole at an angle of substantially 90 degrees to the surface of a plane tangent to the cranium.

Once the catheter is placed in the ventricles of the patient's cranium, the insert 117 is disengaged from the base 110, thus separating the two components. The base 110 is removed from the catheter using the side base opening 122 and leg space 121 (through base slot 126). The insert 117 is then disengaged from the catheter by breaking the insert along the break-away line 124 by pressing the wings 125 together. This causes the insert 117 to break apart allowing the insert to be removed from the catheter, while the catheter remains in the ventricles of the patient's cranium.

Thus, the catheter guide 100 comprises a tubular member 117 defining a tubular channel 132 to permit the passage therethrough of a catheter (not shown), and a base 110, having a side base opening 122 that is contiguous with the slot 120 of the tubular member 117 when the base 110 is connected to the tubular member 117 to form the catheter guide 100. The tubular member 117 further comprises a fracture line 124 extending along the entire length or height of the tubular member 117, and two wings 125 attached on either side of the fracture line 124, whereby after the tubular member 117 is separated from the base 110 and the two wings 125 are pressed together a separation is formed in the tubular member 117 along the fracture line 124, thus allowing the catheter guide 100 to be separated from the catheter.

The embodiment shown in FIGS. 4A and B through 6A and B has advantages, including but not limited to, the simplified removal of the catheter guide from the ventricular catheter. By allowing the insert 117 to be broken off the catheter, it can be removed without disturbing the correct placement of the catheter. The insert can be made with different lumen sizes thus assuring that the catheter is correctly placed. Furthermore, the insert is totally independent of any additional features that may be attached to the catheter (such as cerebral profusion instrumentation or intracranial pressure monitoring equipment). Also, by making the insert breakable, the device is guaranteed to be a single use thus preventing re-use and the concomitant risk of cross infection of patients. Additionally, there are cost savings realized by use of the embodiment shown in FIGS. 4A and B through 6A and B. The cost of manufacture of this device is similar to multiple insert catheter guides. However, the advantage of being able to use it with any catheter reduces inventory costs and makes it a feasible item to keep in inventory.

Figure 8:
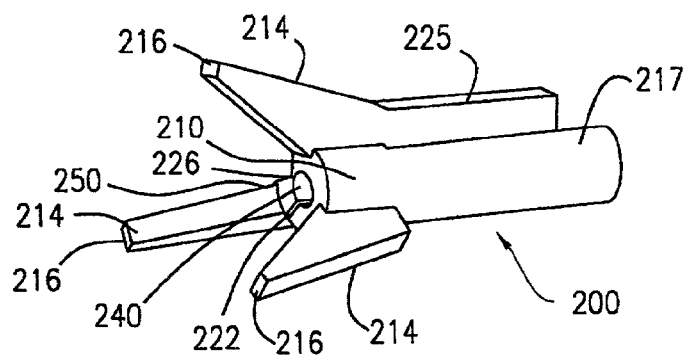
FIG. 8 is a perspective view of the embodiment of the integrated break-away catheter guide of FIG. 7.
Figure 9:
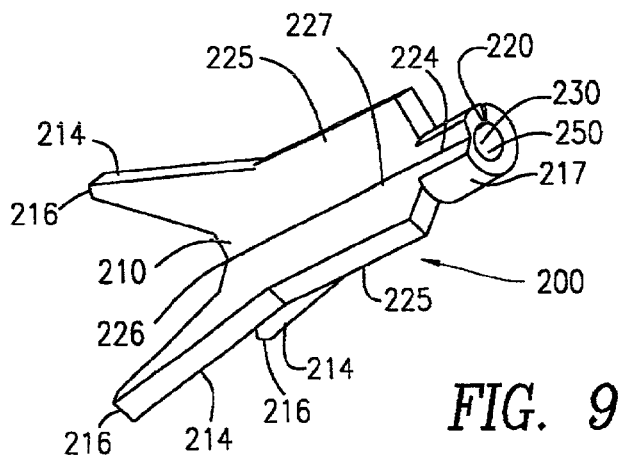
FIG. 9 is another perspective view of the embodiment of the integrated break-away catheter guide of FIG. 7.
Figure 10:
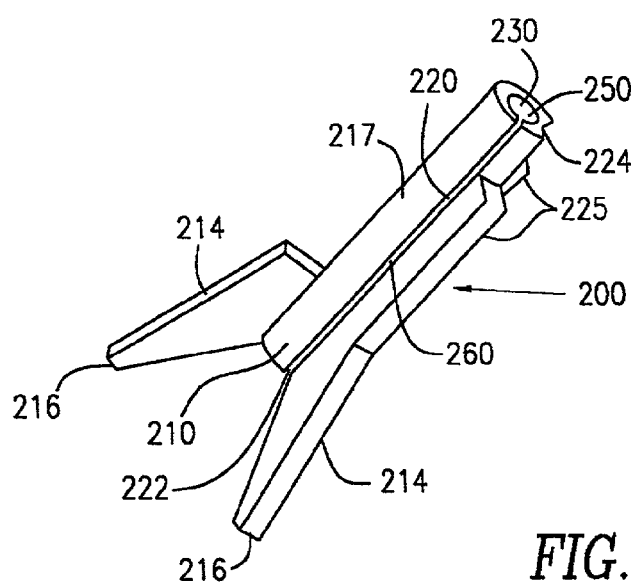
FIG. 10 is still another perspective view of the embodiment of the integrated break-away catheter guide of FIG. 7.

Turning now to FIGS. 7 through 9, an integrated break-away catheter guide 200 is shown. In this embodiment the insert or tubular member 217 and the base 210 are molded as one integral piece, as was described above with respect to the integrated catheter guide 10. The integrated break-away catheter guide 200 may be formed of the same material as that described with respect to catheter guide 10. The catheter guide 200 is equipped with legs or with cone-shaped support with cut-out instead of legs, also as described above with respect to the integrated catheter guide 10. In a preferred embodiment extending from base 210 in a diverging manner are three legs 214. The free ends 216 of legs 214 define a triangle lying within a defined plane.

The base 210 has a base fracture line 226 and the tubular member 217 has a tubular member fracture line 227 that are contiguous. Thus, the catheter guide 200 has a fracture line or the break-away line 224 comprised of the base fracture line 226 and the tubular fracture line 227 that extends through the length or height of tubular member 217 and the base 210. The break-away line 224 is a line, groove or indentation along which the catheter guide 200 may be readily broken into two pieces when the two wings 225 are pressed together. The tubular member 217 is equipped with two wings 225 in the same manner as was described with respect to tubular member 117. Thus by pressing the wings 225 on the insert or tubular member 217 not only does the insert or tubular member 217 split but also the base 210 splits, allowing the catheter guide 200 to be disengaged from the catheter.

Thus, turning to FIG. 7, the catheter guide 200 comprises a tubular member 217 defining a tubular guide hollow 230 extending along its entire height or length to permit the passage therethrough of a catheter (not shown), and a base 210, supporting the tubular member 217, wherein the base 210 has a base hollow 240 extending along its entire height or length to permit the continued passage therethrough of a catheter inserted through the tubular guide hollow. The base 210 may be molded or otherwise integrally attached to the tubular member 217, such that the base 210 and tubular member 217 form one integrated piece and the tubular guide hollow 230 and base hollow 240 are contiguous and form a catheter guide hollow 250 and allow for the insertion of a catheter therethrough. The catheter guide hollow 250 must be of sufficient width to allow for the insertion of the catheter and must not be too large such that the catheter is not held in its proper position.

The base 210 has a base slot 222 extending along its entire height or length and the tubular member 217 has a guide slot 220 extending along its entire height or length such that the base slot 222 is contiguous with the guide slot 220 to form a contiguous common guide slot 260.

Thus, the base 210 and tubular member 217 form one contiguous piece whereby the base 210 is integrated to the tubular member 217 to form the catheter guide 200. The catheter guide 200 controls for angle of entry of a catheter into the human cranium at substantially 90 degrees, as stated above with respect to the catheter guide 10 and the catheter guide 100. Thus, when catheter guide 200 is placed on the patient's cranium with the free ends 216 of legs 214 resting thereupon, the plane of the triangle defined by free ends 216 coincides with or is parallel to a plane tangent to the cranial surface directly below tubular member 217. Accordingly, when a catheter (not shown) is placed within the catheter guide hollow 250, the catheter guide 200 directs the catheter perpendicular to this tangential plane, ensuring its entry into the burr hole through the cranial bone at an angle of substantially 90 degrees to the surface of a plane tangent to the cranium. This alignment assures that a ventricular catheter inserted into a brain in a direction perpendicular to the curvature of the cranium, will not deviate from a preferred course.

The tubular member 217 has a tubular fracture line 227 extending along its entire height or length and two wings 225 attached on either side of the tubular fracture line 227. The base 210 further comprises a base fracture line 226 contiguous with the tubular fracture line 227. Therefore, pressing on the wings 225 of the tubular member 217 splits apart the tubular member 217 and the base 210, respectively, along the tubular fracture line 227 and the base fracture line 226 and because of the existence of the common guide slot 260, the catheter guide splits into two pieces, from the fracture line 224 to the common guide slot 260, allowing the catheter guide 200 to be separated from the catheter. The width of the common guide slot 260 is not critical since the function of the common guide slot 260 in catheter guide 200 is to provide a length of separation along the height or length of the tubular member 217 and base 210 that allows the catheter guide 200 to be broken apart when the two wings 225 are pressed together causing a separation along the break-away line 224.

Turning to FIG. 11, a two-piece connectible catheter guide 300 is shown. In this embodiment, as further shown in FIGS. 12 and 13, an insert or tubular member 317 and a base 310 are two distinctive pieces, which may be connected together to form catheter guide 300. The catheter guide 300 may be formed of the same material as that described with respect to catheter guide 10.

As shown in FIG. 13, in a preferred embodiment extending from base 310 in a diverging manner are three legs 314. The free ends 316 of legs 314 define a triangle lying within a defined plane. In the same manner as described above with respect to catheter guides 10 and 100, when the base 310 and tubular member 317 are connected and catheter guide 300 is placed on the patient's cranium with the free ends 316 of legs 314 resting thereupon, the plane of the triangle defined by free ends 316 coincides with or is parallel to a plane tangent to the cranial surface directly below tubular member 317. Accordingly, when a catheter (not shown) is placed within the tubular member 317, the catheter guide 300 directs the catheter perpendicular to this tangential plane, ensuring its entry into the burr hole through the cranial bone at an angle of substantially 90 degrees to the surface of a plane tangent to the cranium.

Figure 18:
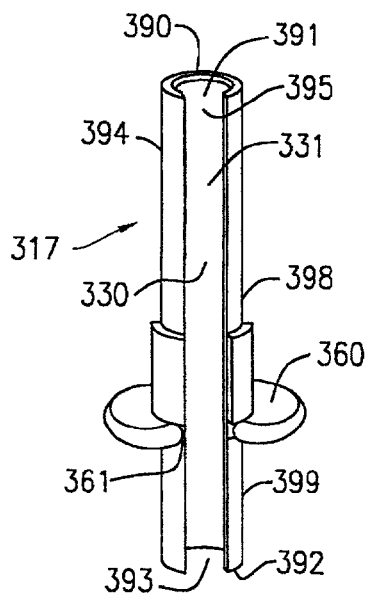
FIG. 18 is a front perspective view of the tubular member of applicants' catheter guide of FIG. 11.
Figure 19:
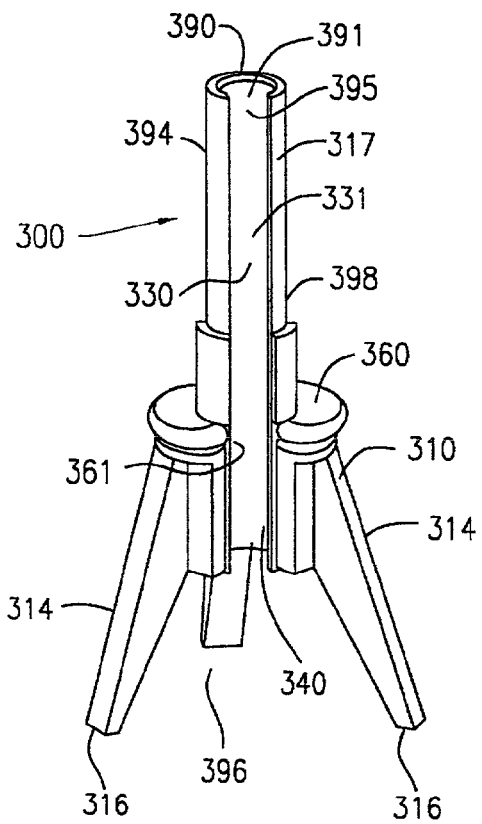
FIG. 19 is a front perspective view of applicants' catheter guide of FIG. 11.

Turning to FIG. 19, the catheter guide 300 comprises the tubular member 317 having a "C" shaped top wall 390 connected to a "C" shaped side wall 394, which is connected to a "C" shaped bottom wall 392. Thus, tubular member 317 defines a central bore 395 along its height or length and also defines a longitudinal slot 331 or opening in its side wall. The diameter of the central bore is not critical but it must, at a minimum, be sufficient to permit the passage of the catheter and it must, at a maximum, not be too large to prevent the catheter from being held in its proper position. The central bore 395 and the longitudinal slot 331 form a tubular guide hollow 330 extending along the entire height or length of the tubular member to permit the passage therethrough of a catheter (not shown). As shown in FIG. 18, the "C" shaped top wall 390 of tubular member 317 forms a top aperture 391 that is contiguous with the tubular hollow 330. The "C" shaped bottom wall 392 of tubular member 317 forms a bottom aperture 393 that is contiguous with the tubular hollow 330. The tubular member 317 may be provided with a platform 360 that separates the tubular member 317 into a top segment 398 and a bottom segment 399. The platform 360 forms a stop that prevents the top segment 398 of the tubular member 317 from descending into a base hollow 340 when the bottom segment 399 of the tubular member 317 is inserted in the base 310. The platform is provided with a slot 361 that is contiguous with the longitudinal slot 331 of the tubular member 317 so as not to interfere with the removal of the tubular member 317 from the catheter.

Figure 17:
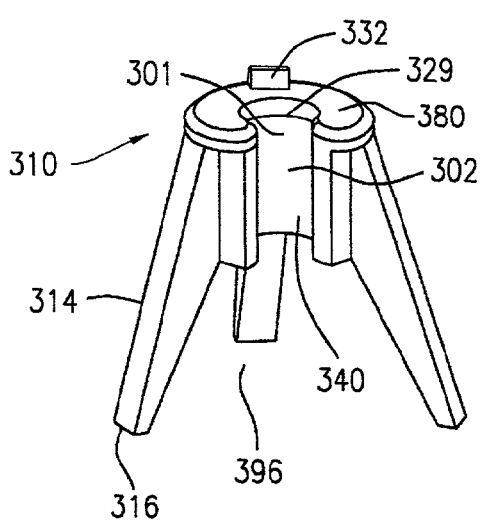
FIG. 17 is a front perspective view of the base of applicants' catheter guide of FIG. 11.

A base 310 supports the tubular member 317. The base 310 has a "C" shaped top wall 380 connected to a "C" shaped side wall 381, which is connected to a "C" shaped bottom wall 382. Thus, as shown in FIG. 17, the base 310 defines a central bore 301 along its height or length and also defines a longitudinal slot 302 or opening in its side wall. The central bore 301 in the base and the longitudinal slot 302 in the base form the base hollow 340 extending along the entire height of the base. The bottom segment 399 of the tubular member 317 may be inserted into the central bore 301 of the base. The base 310 is attachable to the tubular member 317 so that the longitudinal slot 302 of the base may be aligned with the longitudinal slot 331 of the tubular member 317. Thus, a catheter may be passed in or out of the longitudinal slot 331 of the tubular member 317 when the tubular member 317 is seated in the base 310 and the longitudinal slot 302 of the base is aligned with the longitudinal slot 331 of the tubular member.

As illustrated in FIG. 19, the longitudinal slot 302 of base 310 is between two of the legs 314. The longitudinal slot 302 of the base 310 is of sufficient size to allow the removal of all catheters through it easily. Between the two legs, one on each side of the longitudinal slot 302 of the base 310, a leg space 396 is formed. Thus, the longitudinal slot 302 of the base 310 and the leg space 396 form a contiguous space with each other.

Tubular member 317 acts as a guide means for guiding the catheter in a direction perpendicular to the place defined by the triangle formed by legs 314 and through the geometric center thereof Tubular member 317 extends through base 310 in a direction perpendicular to the triangular plane described above, when the base 310 and tubular member 317 are connected. In the same manner, as described above with respect to catheter guide 100, when catheter guide 300 is placed on the patient's cranium with the free ends 316 of legs 314 resting thereupon, the plane of the triangle defined by free ends 316 coincides with or is parallel to a plane tangent to the cranial surface directly below tubular member 317. Accordingly, when a catheter (not shown) is placed within the tubular channel, the catheter guide 300 directs the catheter perpendicular to this tangential plane, ensuring its entry into the burr hole through the cranial bone at an angle of substantially 90 degrees to the surface of a plane tangent to the cranium. This alignment assures that a ventricular catheter inserted into a brain in a direction perpendicular to the curvature of the cranium will not deviate from a preferred course.

The legs of catheter guide 300 may be formed in the same manner, structure and positioning or with the cone-shaped support with cut-out instead of legs, as that described with respect to catheter guide 10. Also, the height of the assembled catheter guide 300 should be similar to that described for the catheter guide 10.

Thus, in use the base 310 and tubular member 317 are assembled to form the catheter guide 300 by pressing together the base 310 and tubular member 317, the catheter guide 300 is placed on the cranium and the catheter is inserted through the lumen of the tubular member 317. The catheter guide 300 is placed on the patient's cranium in the same manner as that described above with respect to the catheter guide 10 to allow for an alignment that assures that a ventricular catheter is inserted into the burr hole at an angle of substantially 90 degrees to the surface of a plane tangent to the cranium. Once the catheter is placed in the ventricles of the patient's cranium, the catheter guide 300 may be removed from the catheter. Longitudinal slot 331 is of sufficient width to allow for removal of the catheter guide 300 from the catheter. The longitudinal slot 331 also allows for visualization of the catheter in the catheter guide 300.

The longitudinal slot 331 together with the leg space 395 and longitudinal slot 302, allow the neurosurgeon to have direct visual access to the burr hole, as well as the catheter and allow for the removal of the catheter guide 300 from the catheter. Thus, the embodiments shown in FIGS. 11 through 19 are that of a two-piece connectible catheter guide with longitudinal slot. The advantages of the embodiment of the invention shown in FIGS. 11 through 19, include by way of example only, easy removal of the catheter guide 300 from the catheter.

Figure 16:
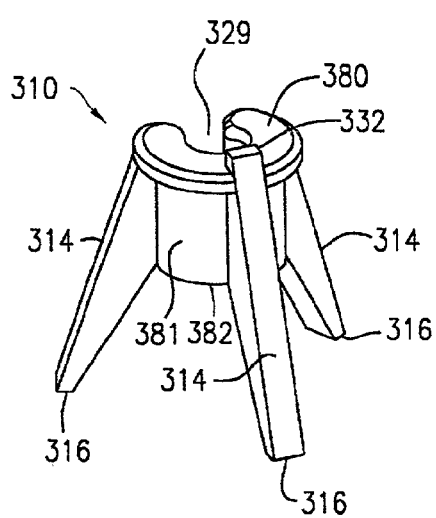
FIG. 16 is a rear perspective view of the base of applicants' catheter guide of FIG. 11.

As shown in FIGS. 13 and 17, the upper "C" shaped top wall 380 of the base forms a top opening 329, which is contiguous with the base hollow 340. The upper "C" shaped top wall 380 may be provided with a protrusion 332. As shown in FIG. 16, the protrusion 332 may be formed as an upper continuation of one of the legs 314, rising above the "C" shaped top wall 380 to from a knob on the top surface of the upper "C" shaped top wall 380.

Figure 14:
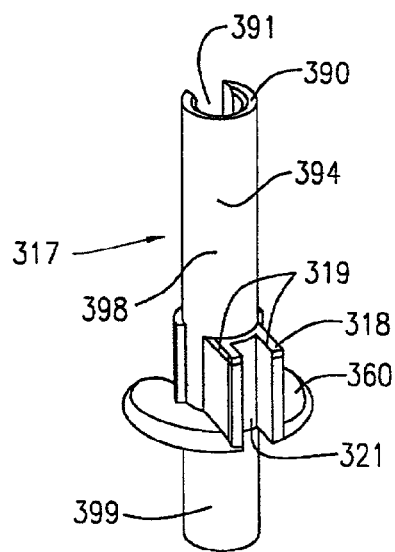
FIG. 14 a rear perspective view of the tubular member of applicants' catheter guide of FIG. 11.
Figure 15:
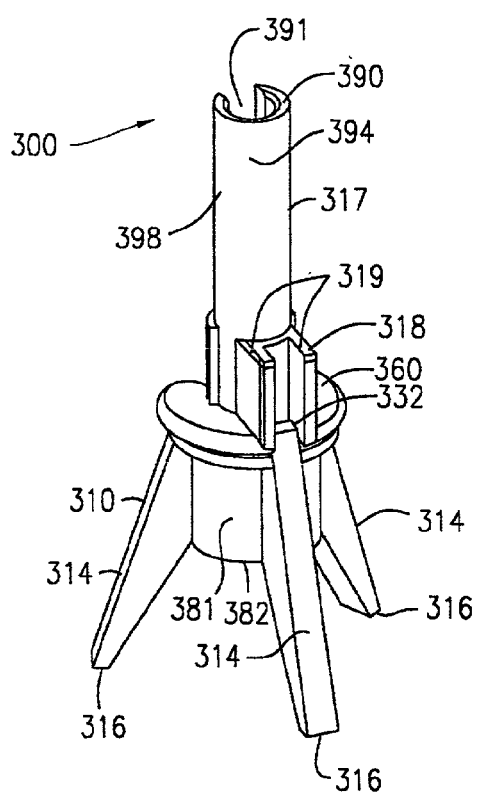
FIG. 15 is a rear perspective view of applicants' catheter guide of FIG. 11.

As shown in FIG. 14, tubular member 317 is provided with a grip 318. Grip 318 preferably comprises a pair of arms 319 that extend outward and may extend substantially perpendicularly to the height of tubular member 317. As shown in FIG. 15, the pair of arms 319 define a space 321 that is sized to mate with protrusion 332. Thus, the protrusion 332 mates with the space 321 to snap together the tubular member 317 to the base 310. The protrusion 332 may be unsnapped from the space 321 to separate the base 310 from the tubular member 317. In use, a surgeon may place his fingers on grip 318 to better hold the tubular member 317.

Thus, there is shown in FIGS. 11 through 19 an embodiment of the present invention a catheter guide 300 for controlling the entry of a ventricular catheter (not shown) at a preferred angle of 90 degrees into a burr hole through the cranium of a patient (not shown). The initial function of catheter guide 300 is to control the angle of entry of the catheter during its insertion into the perforation of the cranium. Catheter guide 300 is formed so base 310 and tubular member 317 are two separate pieces that may be connected by the user pressing the bottom segment 399 of tubular member 317 into the top opening 329 of base 310 and into the central bore 301 of the base 310 so that the side wall 381 of the base 310 securely holds the tubular member 317 in place in the central bore 301 of the base 310. Catheter guide 300 may be seated upon the cranium in the same manner as catheter guide 100.

In use, the base 310 and tubular member 317 are connected to each other by inserting the bottom segment 399 of the tubular member 317 into the central bore 301 of the base 310 so that the bottom segment 399 of the tubular channel 317 lies within the central bore 301 in the base 310, thus forming a passageway for the catheter. In use, the base 310 and tubular member 317 are connected prior to the insertion of a catheter into the catheter guide 300. The catheter guide 300 is placed on the patient's cranium and then a catheter is inserted therethrough.

After use, the catheter guide 300 may be removed from the cranium. The catheter guide 300 may be removed as one piece. The catheter guide 300 may be disengaged from the catheter through the longitudinal slot 331 of the tubular member 317. Thus, the two piece catheter guide 300 has several advantages, for example, allowing for its easy removal from the catheter and for the use of tubular members 317 having different sized lumen. Thus, tubular members 317 may be provided having different size lumen and may be used with base 310.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

The invention claimed is:

1. A catheter guide for controlling an angle of entry of a catheter into a cranium and allowing for ease in removal of the catheter guide from the catheter, said catheter guide comprising a non-deformable tubular member defining a central lumen to permit the passage there through of a catheter, wherein said tubular member has a catheter guide slot along its entire length contiguous with said central lumen, and said catheter guide further comprises a base, said base defining a central lumen for holding the tubular member, whereby the tubular member may be removably inserted in said base, said base has a base slot that may be aligned with the catheter guide slot, whereby said catheter guide may be removed from the catheter through the catheter guide slot, and wherein said base defines a triangle lying within a defined plane, such that when said base and said tubular member are connected and said catheter guide is placed on said cranium, the plane of said triangle is parallel to a plane tangent to said cranium below said tubular member, such that when the tubular member is inserted into said base, said tubular member is in a direction perpendicular to said defined plane and wherein said catheter guide directs an angle of entry of the catheter as substantially 90 degrees into the cranium.

2. A catheter guide, as claimed in claim 1, wherein said tubular member has a platform, whereby the tubular member is prevented from further descending into the central lumen of said base.

3. A catheter guide, as claimed in claim 1, wherein said tubular member has a grip, whereby a user may hold the tubular member.

4. A catheter guide, as claimed in claim 1, wherein said base has a protrusion and said tubular member defines a space for mating with said protrusion whereby said base may be snapped together to said tubular member.

5. A catheter guide, as claimed in claim 1, wherein said base has a cone-shaped support.

6. A catheter guide, as claimed in claim 1, wherein the triangle is equilateral.

7. A catheter guide for controlling an angle of entry of a catheter into a cranium and allowing for ease in removal of the catheter guide from the catheter, said catheter guide comprising a non-deformable tubular member defining a central lumen to permit the passage there through of a catheter, wherein said tubular member has a catheter guide slot along its entire length contiguous with said central lumen, and said catheter guide further comprises a base, said base defining a central lumen for holding the tubular member, whereby the tubular member may be removably inserted in said base, said base has a base slot that may be aligned with the catheter guide slot, whereby said catheter guide may be removed from the catheter through the catheter guide slot, said base has three and only three legs extending therefrom in diverging manner, and said legs define a triangle lying within a defined plane, such that when said base and said tubular member are connected and said catheter guide is placed on said cranium, the plane of said triangle is parallel to a plane tangent to said cranium below said tubular member, such that when the tubular member is inserted into said base, said tubular member is in a direction perpendicular to said defined plane and wherein said catheter guide directs an angle of entry of the catheter as substantially 90 degrees into the cranium.

* * * * *